United States Patent
Kodama

(10) Patent No.: US 9,636,198 B2
(45) Date of Patent: May 2, 2017

(54) DENTAL WHITENING SYSTEM

(71) Applicant: J-Network, Inc., Huntington Beach, CA (US)

(72) Inventor: Akira Kodama, Huntington Beach, CA (US)

(73) Assignee: J-Network, Inc., Huntington Beach, CA (US)

( * ) Notice: Subject to any disclaimer, the term of this patent is extended or adjusted under 35 U.S.C. 154(b) by 156 days.

(21) Appl. No.: 14/620,376

(22) Filed: Feb. 12, 2015

(65) Prior Publication Data

US 2016/0235511 A1   Aug. 18, 2016

(51) Int. Cl.
A61C 17/00 (2006.01)
A61C 19/06 (2006.01)

(52) U.S. Cl.
CPC ............ A61C 19/066 (2013.01); A61C 19/06 (2013.01); A61C 19/063 (2013.01)

(58) Field of Classification Search
CPC ...... A61C 19/06; A61C 19/066; A61C 19/063
USPC ...................................... 433/32, 224, 25, 18
See application file for complete search history.

(56) References Cited

U.S. PATENT DOCUMENTS

| | | |
|---|---|---|
| 6,102,705 A | 8/2000 | Darnell |
| 6,616,447 B1 | 9/2003 | Rizoiu et al. |
| 6,976,841 B1 | 12/2005 | Osterwalder |
| 7,331,784 B2 | 2/2008 | Suzuki |
| 8,172,570 B2 | 5/2012 | Baughman |
| 8,371,853 B2 | 2/2013 | Levine |
| 8,613,616 B2 | 12/2013 | Rose et al. |
| 2007/0015112 A1* | 1/2007 | Hochman ............... A61B 8/546 433/215 |
| 2008/0008978 A1* | 1/2008 | Conrad .................. A61C 19/06 433/32 |
| 2008/0044796 A1 | 2/2008 | Hsu |
| 2008/0063999 A1 | 3/2008 | Osborn |
| 2008/0233541 A1 | 9/2008 | De Vreese et al. |
| 2012/0214122 A1 | 8/2012 | Dwyer et al. |

FOREIGN PATENT DOCUMENTS

| | | |
|---|---|---|
| EP | 1741407 | 1/2007 |
| EP | 2386264 | 11/2011 |
| WO | WO 99 37236 | 1/1999 |
| WO | WO 2010 040980 | 9/2009 |
| WO | WO2011/155374 | 12/2011 |
| WO | WO2013/172602 | 11/2013 |

* cited by examiner

Primary Examiner — Michael Carey
(74) Attorney, Agent, or Firm — Eric Karich; Karich & Associates

(57) ABSTRACT

A dental whitening system has a removable heating component that includes a heating plate having a heat generator. A positioning element, such as a dental tray, is used to position the removable heating component inside the person's lips, over and proximate to the person's teeth, so that heat from the heating plate is directed to the person's teeth.

11 Claims, 4 Drawing Sheets

DENTAL WHITENING SYSTEM

BACKGROUND OF THE INVENTION

Field of the Invention

This invention relates generally to dental whitening systems, and more particularly to a dental whitening system that includes a removably heat plate for accelerating a whitening process used for whitening teeth.

Description of Related Art

Conventional teeth whitening is often performed in a dental office, and can take hours, the process may be painful, and is fairly costly. The best whitening results are achieved using 15 to 35 percent hydrogen peroxide gels, sometimes coupled with a high intensity light in the 300-990 nm range to expedite the bleaching chemical reaction. The results tend to fade within 1-2 weeks, however, leaving patients dissatisfied with the benefits relative to the time and expense.

Over-the-counter products may be purchased for use at home, to avoid the need to meet with a dentist. These systems include mouthpieces that use a whitening agent such as 10-20 percent carbamide peroxide gels or up to 8 percent hydrogen peroxide that also contain glycerin, carbomer or carbamide, sodium hydroxide, water, and flavoring agents. Some gels that contain more than 10 percent carbamide peroxide will also include sodium fluoride to reduce sensitivity and strengthen teeth. Over-the-counter products suffer from other deficiencies, such as difficulty of use, irritation to the fingers and results usually take seven to ten days. Often, there is only minimal improvement. The consumer needs a customizable whitening alternative that yields results similar to the initial professional whitening, but at the convenience of the home that allows for frequency applications and a more stabilized whitening result.

One example of an at-home system is shown in Rizoiu et al., U.S. Pat. No. 6,616,447, which teaches a dental whitening device that includes a dental tray that includes a plurality of LEDs for directing electromagnetic radiation onto the user's teeth. The LEDs are integrally mounted in the dental tray, and function to increase the effectiveness of the whitening agents used.

Similarly, Carnell, U.S. Pat. No. 6,102,705, teaches a similar dental tray with heating elements disposed integrally therein. The heating elements are integral with the dental tray, and cannot be removed from the dental tray, or used with another dental tray.

The problem with these prior art devices is that the LED components and the heating components are integrally mounted within the dental tray. There is a long-felt need in the art for an improved design that does not include this approach. The present invention teaches a dental whitening system that includes heating elements, and optionally also LEDs, that are mounted on a heating plate that is adapted to be removably mounted on a dental tray. The present invention fulfills these needs and provides further advantages as described in the following summary.

SUMMARY OF THE INVENTION

The present invention teaches certain benefits in construction and use which give rise to the objectives described below.

The present invention provides a dental whitening system that is adapted to be positioned adjacent the person's teeth for whitening the person's teeth. The dental whitening system comprises a removable heating component that includes a heat generator for generating heat. A positioning element, such as a dental tray, is used to position the removable heating component inside the person's lips, over and proximate to the person's teeth, so that heat from the heating plate is directed to the person's teeth.

A primary objective of the present invention is to provide a dental whitening system having advantages not taught by the prior art.

Another objective is to provide a dental whitening system that includes a removable heating component that may be readily removed from a dental tray, so that the removable heating component may be used with different dental trays, or without a dental tray altogether, if so desired.

Another objective is to provide a dental whitening system that applies a suitable amount of heat onto the person's teeth, without burning the person, or causing discomfort.

Another objective is to provide a dental whitening system that provides superior whitening results with less time and discomfort.

A further objective is to provide a dental whitening system that is easy to use, easy to clean and maintain, and easy to store.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present invention. In such drawings.

DETAILED DESCRIPTION OF THE INVENTION

The above-described drawing figures illustrate the invention, a dental whitening system 10 for accelerating a whitening of the person's teeth 14. The dental whitening system 10 is adapted for use with a whitening gel (e.g., a hydrogen peroxide gel, or similar composition) that chemically whitens the person's teeth 14. As discussed in greater detail below, the dental whitening system 10 applies heat, and optionally also electromagnetic radiation, to the person's teeth 14, to enhance the effectiveness of the whitening gel.

Figure 1:
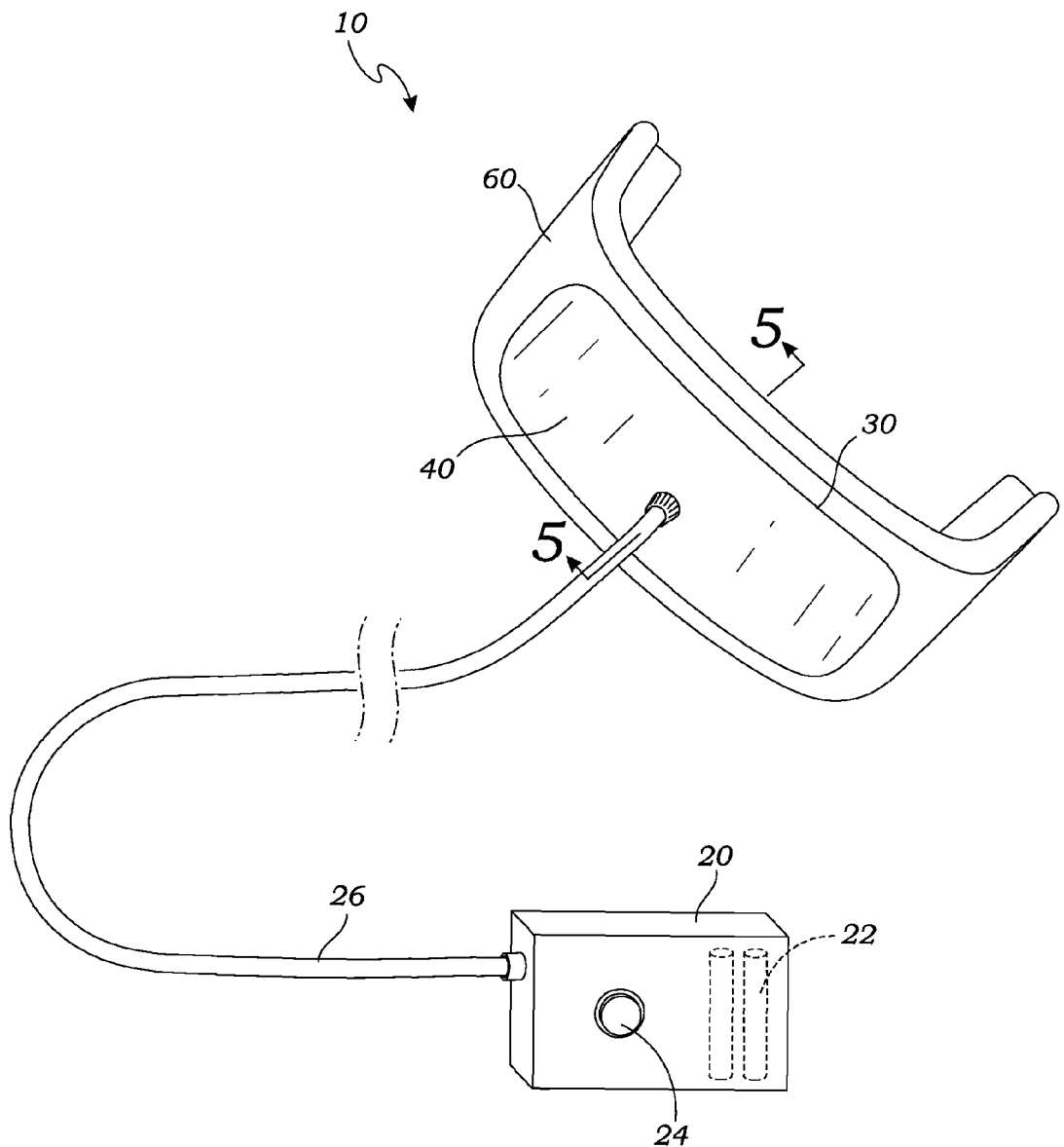
FIG. 1 is a perspective view of a dental whitening system according to one embodiment of the present invention that includes a dental tray and a removable heating component.

FIG. 1 is a perspective view of a first embodiment of the dental whitening system 10. As shown in FIG. 1, the dental whitening system 10 may include a removable heating component 40 that is used to enhance the effectiveness of whitening gel. In this embodiment, the dental whitening system 10 includes a control unit 20 that includes a power source 22, in this case a battery (or batteries), and a switch 24 for providing power to the removable heating component

40. An electrically conductive power cord 26 may operably connect the control unit 20 with the removable heating component 40.

In alternative embodiments, the power source 22 may be any alternative power source (e.g., AC power socket, etc.) known in the art. Also, the heating plate 42 may be heated using alternative devices and methods. For example, in one alternative embodiment, the removable heating component 40 itself may include the power source 22 (e.g., a rechargeable battery) that may be charged by a charging station (not shown) when not in use. In another embodiment, the removable heating component 40 may be electrically connected to an AC plug that may be plugged into a household socket. These alternative embodiments, and other alternatives known to those skilled in the art, are also considered within the scope of the present invention.

Figure 3:
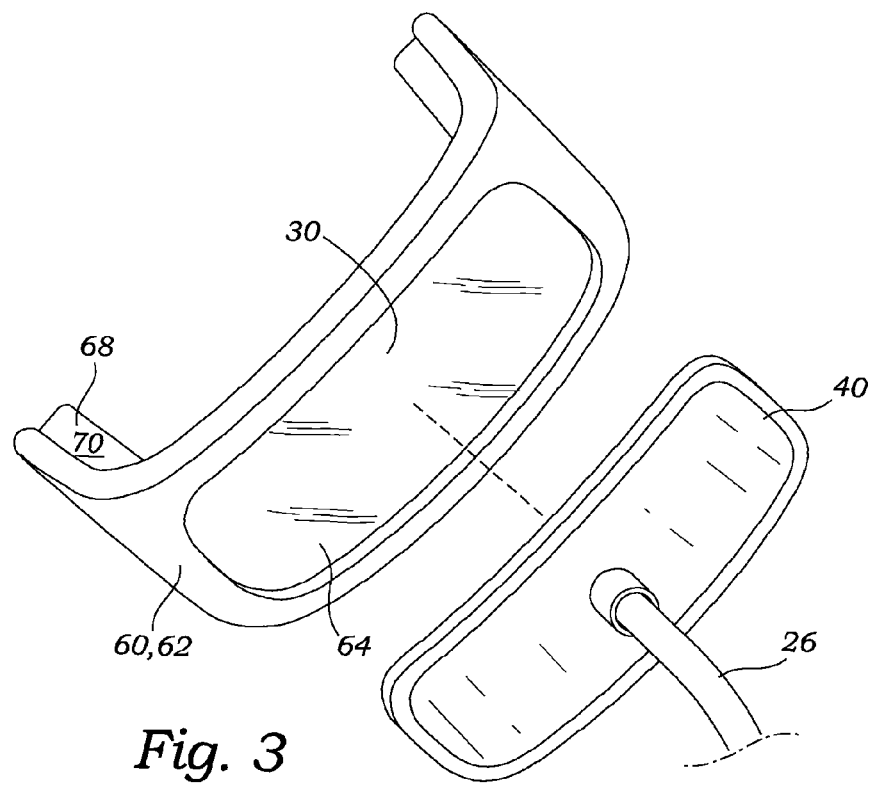
FIG. 3 is an exploded perspective view of the removable heating component being inserted into the dental tray.
Figure 4:
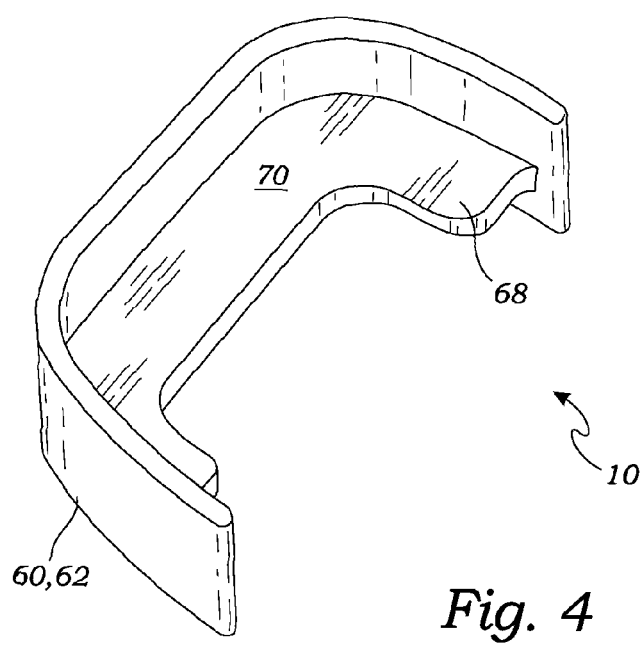
FIG. 4 is a rear perspective view of the dental tray.

The dental whitening system 10 may further include a positioning element 30 for positioning the removable heating component 40 between a person's lips 12 and teeth 14 and adjacent a dental tray 60 that includes the whitening gel (as shown in FIG. 4). In the present embodiment, the positioning element 30 is provided by a heating component recess in the dental tray 60. The heating component recess 30 is shaped and sized for removably mounting the removable heating component 40 in the proper position and orientation, such that the removable heating component 40 may be readily removed and kept separate from the dental tray 60. The heating component recess 30 is shown more clearly in FIGS. 3-4, and discussed in greater detail below. The construction of the dental tray 60 and other optional embodiments are also discussed in greater detail below.

While this first embodiment of the positioning element 30 is illustrated, alternative embodiments of the positioning element 30 may also be used. Those skilled in the art may devise alternative brackets, holders, and the like, whether part of the dental tray 60 or not, for operatively positioning the removable heating component 40 as described herein. These alternative embodiments should also be considered within the scope of the present invention.

Figure 2:
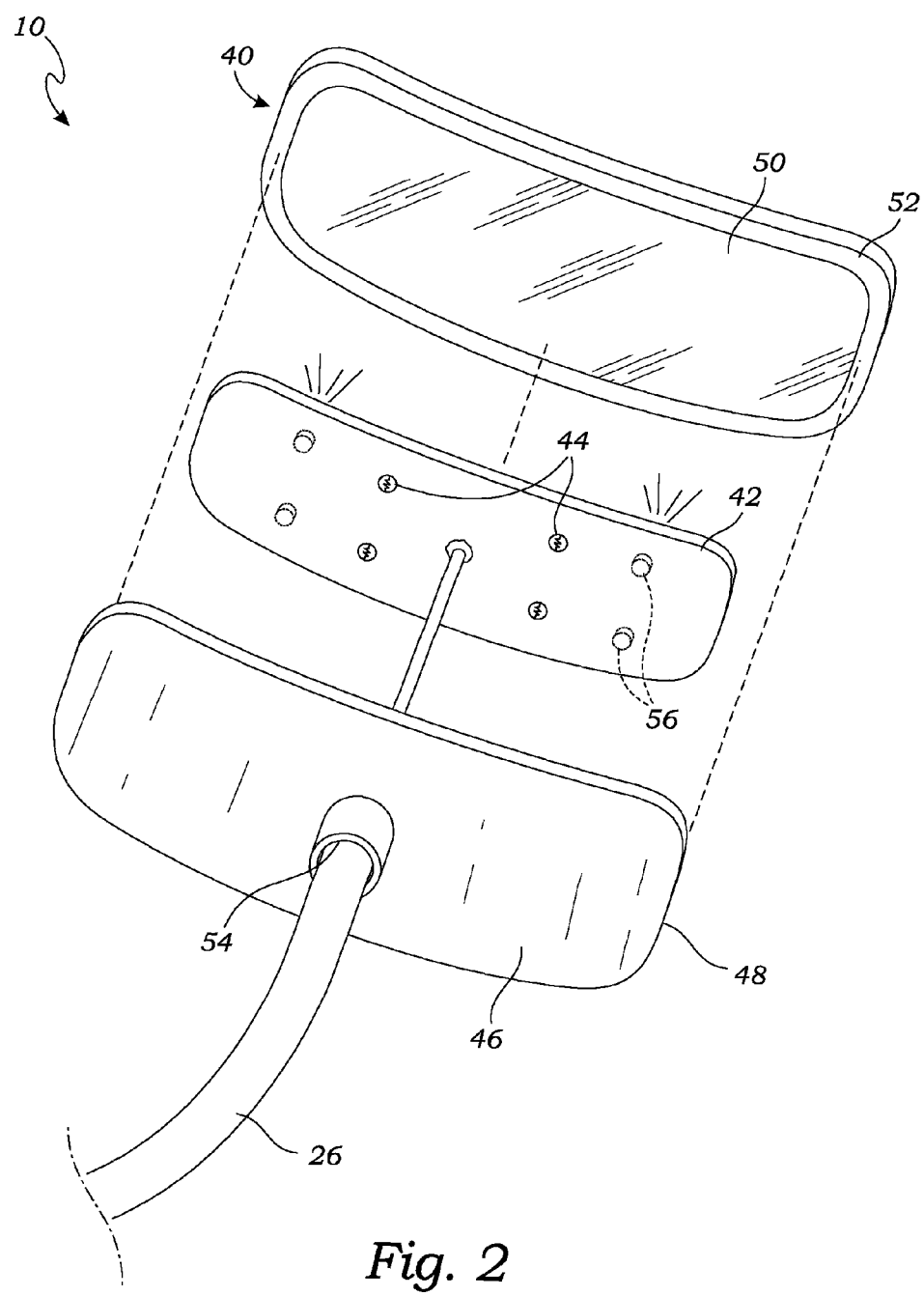
FIG. 2 is an exploded perspective view of the removable heating component of the dental whitening system, illustrating internal components of the removable heating component.

FIG. 2 is an exploded perspective view of one embodiment of the removable heating component 40, illustrating internal components of the removable heating component 40. In this embodiment, the removable heating component 40 includes a generally rectangular heating plate 42 that is sized and shaped to fit over the person's teeth 14. For purposes of this application, the term "generally rectangular" include any form or shape that approximates a rectangular construction, regardless of the particular sides formed, angles formed, and curves incorporated.

The heating plate 42 includes a heat generator 44 for generating heat. In this embodiment, the heat generator 44 includes a plurality of resistive heating elements 44 disposed in spaced apart positions around the heating plate 42. Those skilled in the art may devise alternative heat generation devices and methods, and such alternatives are considered within the scope of the present invention.

Heat from the heating elements 44 is transmitted for providing suitable heat to the person's teeth 14 for accelerating the chemical reactions (e.g., from the hydrogen peroxide gel) used to whiten teeth 14. The heating elements 44 functions to increase the effectiveness of the whitening agents used, according to the Q10 rules (i.e., for every 10 degrees C. of increased heat, the reaction rate doubles). The heating elements 44 must therefore be maintained a proper distance from the person's teeth 14, as shown in FIG. 4, so that they are suitably heated for catalyzing the gel reaction, but not overheated to cause discomfort or injury to the person.

In the embodiment of FIG. 2, the removable heating component 40 includes a first cover plate 46 and a second cover plate 50 that together surround and protect the heating plate 42. The first and second cover plates 46 and 50 are sized and shaped to fit between the person's lips 12 and teeth 14, and to fit into and securely engage the positioning element 30 (e.g., the heating component recess).

In this embodiment, the first cover plate 46 includes a first cover perimeter 48 and the second cover plate 50 includes a second cover perimeter 52, and the first and second cover perimeters 48 and 52 are bonded together, preferably forming a watertight seal so that water or other contamination cannot reach the heating plate 42. The first and second cover perimeters 48 and 52 may be bonded together with an adhesive, or during the molding process (e.g., co-molded), heat welding, or in any other manner known to one skilled in the art. While one embodiment is illustrated, those skilled in the art may devise many alternative structures for holding and protecting the heating elements 44, and these alternative structures are considered within the scope of the present invention.

In this embodiment, the electrically conductive power cord 26 that is operatively connected with the power source 22 extends through the first cover plate 46 via an aperture 54, which is also preferably watertight, to operably connect with the heat generator 44.

The heating plate 42 may further include a source of suitable electromagnetic radiation, such as one or more light emitting diodes ("LEDs") 56. In this embodiment, the second cover plate 50 is transparent so that electromagnetic radiation from the LEDs 56 is transmitted to the person's teeth 14 for further accelerating the whitening of the person's teeth 14.

While the present invention illustrates the heating plate 42 as a single unit, it could also be formed in two or more segments. In one embodiment, for example, the heating plate 42 could include a top half and/or a bottom half (not shown) that are associated with the person's top and/or bottom teeth 14. It could also be split vertically into left and/or right sections, or otherwise, depending upon the designs of one skilled in the art, and these and other alternative configurations should be considered within the scope of the present invention.

FIG. 3 is an exploded perspective view of the removable heating component 40 being inserted into the heating component recess 30 of the dental tray 60. As shown in FIG. 3, the heating component recess 30 is sized and shaped to receive and frictionally engage the removable heating component 40. The heating component recess 30 may include an annular lip 32 for retaining the heating plate 42 within the heating component recess 30. While this form of recess 30 is illustrated as one optional embodiment, alternative forms of receivers such as are known in the art or within the skill of one skilled in the art are also considered within the scope of the present invention.

Figure 5:
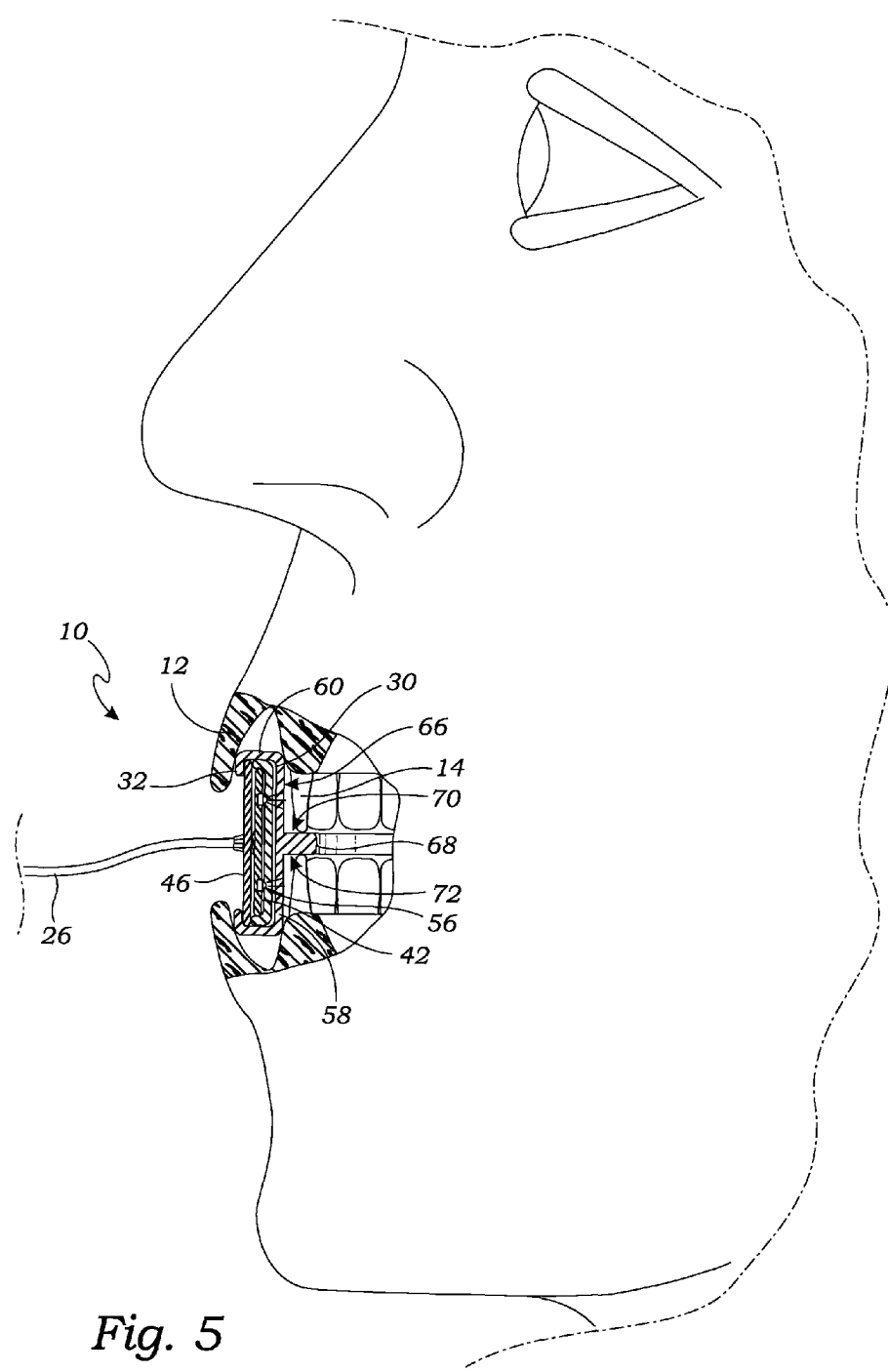
FIG. 5 is a sectional view thereof taken along line 5-5 in FIG. 1, illustrating the removable heating component operably positioned in the dental tray and proximate a person's teeth.

FIG. 4 is a rear perspective view of the dental tray 60 illustrating a bite tab 68. The bite tab 68 has an upper surface 70 and a lower surface 72 (shown in FIG. 5) configured to be clamped between the person's teeth 14 for holding the dental tray 60 (and the removable heating component 40 of FIG. 3) in the person's mouth adjacent the teeth 14, as shown in FIG. 5. The dental tray 60 is discussed in greater detail below.

FIG. 5 is a sectional view thereof taken along line 5-5 in FIG. 1, illustrating the removable heating component 40 operably positioned in the dental tray 60, between the person's lips 12 and teeth 14, so that the heating elements 44 are proximate the person's teeth 14. As shown in FIGS. 1-5, in this embodiment the dental whitening system 10 is used in conjunction with the dental tray 60 mentioned above. The dental tray 60 of this embodiment includes a generally U-shaped body 62 that includes a center portion 64 that includes the heating component recess 30. The dental tray 60 includes an inner surface 66 shaped to be positioned adjacent the person's teeth 14, and includes the bite tab 68 that extends rearward from the inner surface 66. The basic construction of the dental tray 60 is known in the art, and is therefore not discussed in greater detail herein.

In this embodiment, the center portion 64 of the heating component recess 30 is transparent, so that the LEDs 56 of the heat plate may direct electromagnetic radiation onto the person's teeth 14.

As best shown in FIGS. 1-5, the removable heating component 40, which in this case includes the heating plate 42 and the first and second cover plates 46 and 50, fits into and frictionally engages the heating component recess 30 of the dental tray 60. When the removable heating component 40 is positioned within the heating component recess 30 of the dental tray 60, the heating plate 42 is operably positioned adjacent the person's teeth 14, inside of the person's lips 12, for applying heat to the person's teeth 14, and thus accelerating the whitening process. The removable heating component 40 may also be removed from the dental tray 60, as shown in FIG. 1, either for use with another dental tray 60, or for storage, shipping, maintenance, etc.

As used in this application, the words "a," "an," and "one" are defined to include one or more of the referenced item unless specifically stated otherwise. Also, the terms "have," "include," "contain," and similar terms are defined to mean "comprising" unless specifically stated otherwise. Furthermore, the terminology used in the specification provided above is hereby defined to include similar and/or equivalent terms, and/or alternative embodiments that would be considered obvious to one skilled in the art given the teachings of the present patent application.

What is claimed is:

1. A dental whitening system that is adapted to be positioned between a person's lips and teeth for accelerating a whitening of the person's teeth, the dental whitening system comprising:
    a dental tray shaped to fit over the person's teeth, the dental tray having an inner surface, the dental tray further comprising a bite tab that extends rearward from the inner surface, the bite tab having an upper surface and a lower surface configured to be clamped between the person's teeth for holding the dental tray in the person's mouth such that that the inner surface is positioned against the person's teeth;
    a removable heating component that includes a heating plate that includes a heat generator for generating heat; and
    a heating component recess formed in the dental tray opposite the inner surface, the heating component recess having an annular lip that functions to frictionally engage the removable heating component for removably retaining the heating plate within the heating component recess, such that heat from the removably heating component is transmitted through the dental tray to the person's teeth.

2. The dental whitening system of claim 1, further comprising:
    a control unit that includes a battery and a switch; and
    an electrically conductive power cord operably connecting the heat generator with the battery of the control unit through the switch, without contacting the dental tray.

3. A dental whitening system for accelerating a whitening of a person's teeth, the dental whitening system comprising:
    a dental tray having an inner surface shaped to be positioned adjacent the person's teeth, and a bite tab that extends rearward from the inner surface, the bite tab having an upper surface and a lower surface configured to be clamped between the person's teeth;
    a removable heating component that includes a heat generator for generating heat; and
    a heating component recess formed in the dental tray opposite the inner surface for removably receiving the removable heating component and for operably positioning the removable heating component proximate to the person's teeth, such that heat from the removably heating component is transmitted through the dental tray to the person's teeth.

4. The dental whitening system of claim 3, wherein the dental tray includes a generally U-shaped body that includes a center portion that includes the heating component recess.

5. The dental whitening system of claim 3, wherein the heating component recess includes an annular lip for retaining the removable heating component within the heating component recess, and wherein a rear wall of the heating component recess is transparent.

6. The dental whitening system of claim 3, wherein the removable heating component includes a first cover plate and a second cover plate that together surround a heating plate, and wherein the heat generator is operably mounted on the heating plate between the first and second cover plates.

7. The dental whitening system of claim 6, wherein the first cover plate includes a first cover perimeter and the second cover plate includes a second cover perimeter, and the first and second cover perimeters are bonded together.

8. The dental whitening system of claim 7, wherein the first and second cover perimeters are bonded together to form a watertight seal so that the heat plate is protected from contamination during use.

9. The dental whitening system of claim 6 wherein the heat plate further includes a plurality of LEDs, and wherein the second cover plate is transparent.

10. The dental whitening system of claim 3, further comprising an electrically conductive power cord that is operatively connected with a power source and extends through the first cover plate to operably connect with the heat generator.

11. A method for whitening a person's teeth, the method comprising the steps of:
    providing a dental tray having an inner surface, and a bite tab that extends rearward from the inner surface, the bite tab having an upper surface and a lower surface, the dental tray further comprising a heating component recess formed in the dental tray opposite the inner surface;
    positioning the dental tray adjacent the person's teeth;
    clamping the bite tab of the dental tray between the person's teeth;
    providing a removable heating component that includes a heat generator for generating heat;
    positioning the removable heating component in the heating component recess such that heat from the removably heating component is transmitted through the dental tray to the person's teeth; and generating heat in the removably heating component via the heat generator, such that the heat passes through the dental tray to the person's teeth.

\* \* \* \* \*